United States Patent [19]

Pedotti

[11] 4,136,682

[45] Jan. 30, 1979

[54] APPARATUS PARTICULARLY FOR EVALUATING THE FUNCTIONALITY OF MAN LOCOMOTIVE FACULTIES

[76] Inventor: Antonio Pedotti, Via Garebaldi 4, Brenta (Varese), Italy

[21] Appl. No.: 719,030

[22] Filed: Aug. 30, 1976

[30] Foreign Application Priority Data

Sep. 4, 1975 [IT] Italy .................... 26912 A/75

[51] Int. Cl.² .................................... A61B 5/10
[52] U.S. Cl. .................... 128/2 S; 73/172
[58] Field of Search .......... 128/25, 80 DB, 80 G; 177/210 C; 73/379, 172; 346/33 M

[56] References Cited

U.S. PATENT DOCUMENTS

| | | | |
|---|---|---|---|
| 2,290,387 | 7/1942 | Schwartz | 346/33 ME |
| 3,090,226 | 5/1963 | Corti | 73/141 A |
| 3,169,022 | 2/1965 | Kretsinger | 177/210 C |
| 3,712,294 | 1/1973 | Muller | 128/2 S |
| 3,826,145 | 7/1974 | McFarland | 128/2 S |
| 3,894,437 | 7/1975 | Hagy et al. | 128/2 S |
| 3,906,931 | 9/1975 | Terekhov | 128/2 S |

FOREIGN PATENT DOCUMENTS

| | | | |
|---|---|---|---|
| 1918521 | 11/1969 | Fed. Rep. of Germany | 128/2 S |
| 1002866 | 9/1965 | United Kingdom | 128/2 S |

OTHER PUBLICATIONS

"Kistler System Manual", Kistler Instruments, AG/CH 8408 Winterthur, Switzerland 1974 pp. 1-5, 1972 pp. 1-2.

Cappozzo, A. et al. "A General Computing Method for the Analysis of Human Locomotion", J. Biomech. 9/75 V. 8 pp. 307-320.

Primary Examiner—Robert W. Michell
Assistant Examiner—Francis J. Jaworski
Attorney, Agent, or Firm—Guido Modiano; Albert Josif

[57] ABSTRACT

It is described a man locomotive functionality evaluating apparatus comprising a rigid platform adapted to support a subject walking thereonto and exercising on it a force and/or pressure due to said walking; a plurality of force and/or pressure transducing members operatively associated with the platform for providing electric signals representative of the force and/or pressure on the platform and a hybrid processor circuitally connected to said transducing members and adapted to in-line converting on output display means the time-space representation of the projection on a plane of the resultant of the forces and/or pressures acting on the platform.

2 Claims, 5 Drawing Figures

APPARATUS PARTICULARLY FOR EVALUATING THE FUNCTIONALITY OF MAN LOCOMOTIVE FACULTIES

BACKGROUND OF THE INVENTION

The present invention relates to an apparatus particularly for evaluating the functionality of man locomotive faculites. More specifically, the present invention relates to an apparatus adapted to provide, by means of a simple test to be conventionally carried out in the clinical practice, a quantitatively exact recording of the man locomotive faculty conditions.

As it is known, the man locomotive apparatus is of basical importance for the man relational life and it is frequently subjected to lesions of various nature. Actually no device is known which is able to provide an exact and reliable recording of the man locomotive apparatus in order to realize methods and instruments adapted to be used for recovering the functionality thereof.

In fact, though there are known several recording methods based on cinematographic and stroboscopic téchniques, they are not adapted to provide a meaningful and easily readable recording. Even some recently made attempts for diagnosing the man locomotive functionality by measuring and successively elaborating the vertical and horizontal components of the bearing reaction force due to the walking of a subject on force or effort platforms of known type have not been satisfactory.

SUMMARY OF THE INVENTION

Therefore it is the primary object of the present invention to provide a man locomotive functionality evaluating apparatus able to supply a reliable, quantitatively exact and easily interpretable recording of the man locomotive faculty conditions.

Another object is to provide an evaluating apparatus which is extremely sensitive to possible walk variations caused by functional impairing of the man locomotive faculties.

Another object of the present invention is to provide an apparatus able to supply a reliable, objective and easily interpretable recording of the functional loss caused by damages to the man locomotive system at osseous, muscular, nervous level both of congenital type and due to trauma or diseases.

Another object of the invention is to provide an evaluating apparatus adapted to supply a reliable and easily interpretable recording of the functional recovery following the application of bloody or not-bloody therapies.

Another object of the present invention is to provide an evaluating apparatus adapted to provide a reliable and easily interpretable recording for the development of prostheses.

Another object of the present invention is to provide an evaluating apparatus adapted to in-line provide a reliable and easily interpretable recording for exactly and objectively evaluating the performance of athletes in several fields (racing, high and long jump, etc.) for a better technical-athletic preparation.

The aforesaid and other objects are achieved by a human locomotive functionality evaluating apparatus comprising a substantially rigid platform adapted to support a subject walking thereonto and exercising on said platform a force and/or pressure due to said walking; a plurality of force and/or pressure transducing members operatively associated with said platform and adapted to provide a corresponding multiplicity of electrical signals representative of said force and/or pressure on said platform, said apparatus being characterized in that it further comprises hybrid processing or calculating means circuitally connected to said plurality of transducing members and adapted to in-line converting onto output display means the time-space representation of the projection on a plane of the resultant of the forces and/or pressures acting on said platform due to said walking of said subject thereonto.

BRIEF DESCRIPTION OF THE DRAWING

Further characteristics and advantages of the present invention will become apparent from the following description of a preferred embodiment of the invention illustrated as an example only in the drawings in which.

DESCRIPTION OF THE PREFERRED EMBODIMENTS

Figure 1A:
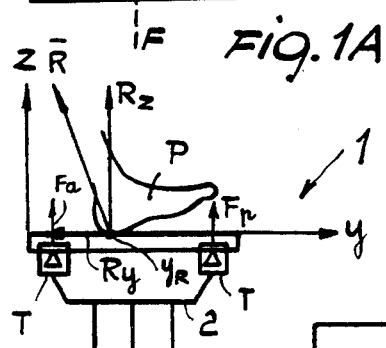
FIG. 1A is a schematic explicative view useful for understanding the present invention.
Figure 1:
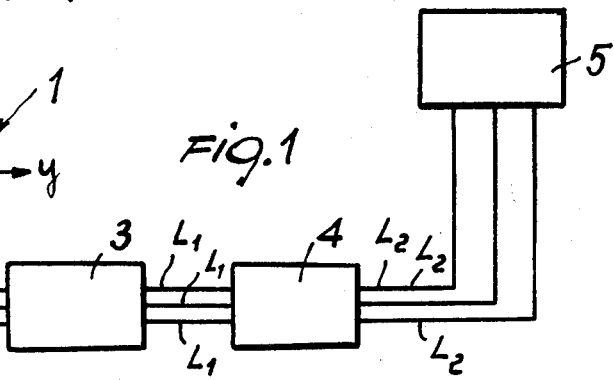
FIG. 1 is a schematic view of an embodiment of the evaluating apparatus according to the present invention.

Referring to the drawings, and particularly to FIG. 1, one preferred embodiment of the inventive evaluating apparatus is shown and indicated by the reference number 1. The apparatus 1 comprises a substantially rigid platform 2 of known type and easily available on the market adapted to receive thereonto a subject to be examined, of which only a foot P is shown. Fixedly associated with the platform 2 there are force and/or pressure transducing members T which, in the preferred embodiment, are piezoelectric quartz transducing members which, as it is known for example from "Operating and Service Instructions" by KISTLER Instruments, have high directionality and great precision and are moreover able to provide electrical voltages which are directly related to the force applied thereto. More specifically said quartz transducing members T provide an electrical charge which is proportional to the force applied thereto; said charge variation to an electrical voltage variation. It is to be noted that, although only two transducing members T are shown in FIG. 1 for sake of semplicity, actually in the preferred embodiment four transducing elements are used, said transducing elements being located at the four corners of the platform 2. As it is shown in FIG. 1, the voltage signals at the outputs of the amplifier circuits 3 are fed through leads L1 to a hybrid elaborating means or calculator 4 according to the present invention to be described with reference to FIG. 2 which elaborates said signals to provide in-line, on display means 5 circuitally connected through leads L2 to the hybrid elaborating means or processor 4, a time-space vectorial representation of the projection onto a plane of the resultant of the forces and/or pressures acting on the platform 2 and due to the walking of a subject onto said platform 2.

In order to provide for a better understanding of FIG. 2, the inventive way to obtain a time-space vectorial representation of the forces and/or pressures acting on the platform 2 is described below.

Suppose there are four piezoelectric transducing members T, each of them being able to provide signals which are proportional to the three components $F_{z1}$, $F_{y1}$, $F_{x1}$ of the force acting on said transducing member. These signals may be summed with one another according to several combinations. Suppose that at the output of the platform 2 and of the charge amplifier circuits 3 the following signals are available:

$F_{1z}, F_{2z}, F_{3z}, F_{4z}$ $F_{xT} = F_{1x} + F_{2x} + F_{3x} + F_{4x}$, $F_{yT} = F_{1y} + F_{2y} + F_{3y} + F_{4y}$.

The projection on a plane (for example the z-y plane of FIG. 1) of the dynamic actions exercised by a subject walking on the platform 2 will be a vector $\bar{R}$ (FIG. 1) where R represents the equilibrating force exerted by the platform on the foot as drawn in FIG. 1 is characterized by the amplitude, the slope and the $Y_R$ coordinate of its application point. These parameters are time functions. To provide a time-space representation of the $\bar{R}$ vector on the z-y plane we can operate, according to the present invention, in the following manner:

(a) by suitably locating several switches (which will be further described with reference to FIG. 2) the following quantities may be obtained:

$$F_a = F_{1z} + F_{2z} \quad (I)$$

(designated as the front vertical component of the bearing reactions (see FIG. 1) and $$F_p = F_{3z} + F_{4z} \quad (II)$$

(designated as the rear vertical component of the bearing reactions — FIG. 1) and $$F_{yT} = F_{1y} + F_{2y} + F_{3y} + F_{4y}$$

(designated as the total horizontal component of the bearing reactions — FIG. 1).

(b) After the provision of the quantities $F_a$, $F_b$ and $F_{yT}$, which are time variable, these quantities are discretized into constant time intervals, $\Delta t$, imposed by a clocking device. These intervals and therefore the time sampling frequency, may be predetermined by means of a suitable step device (not shown). For each time period $t_k = K\Delta T$, with $K = 0, 1, 2 \ldots$ the following values may thus be obtained:

$F_a(K\Delta t) \triangleq F_{ak}$ $F_p(K\Delta t) \triangleq F_{pk}$, $F_{yT}(K\Delta t) = F_{yTk}$, which are held for the necessary time by means of a hold circuit of known type. For each time period $K\Delta t$ the hybrid elaborating means provides:

(1) the value of the total vertical component $R_z$ of the R vector given by:

$R_z(K\Delta t) \triangleq R_{zk} = F_{ak} + F_{pk}$ (2) the value of the total horizontal component $R_y$ of the $\bar{R}$ vector given by: $R_y(K\Delta T) \triangleq R_{yk}$ (3) the value of the coordinate of the vector $\bar{R}$ application point $Y_R$ (which is the location at which an equivalent force to $F_a$ and $F_p$ could be placed with an equivalent moment of force) given by: $Y_R(K\Delta T) \triangleq Y_{RK} = [F_{pk}/(F_{ak} + F_{pk})] \cdot L$ where L represents, on a suitable scale, the platform length (more specifically the distance between the front and rear transducing member pair). For each time period $K\Delta t$, the hybrid elaborating means 4 provides, owing to a generation of exponential curves by the driving of a central clocking device, three signals x, y, z. These signals, shown in FIG. 2, represent respectively the point of application of the components of the resultant force along the x-axis, the y-axis and the z-axis respectively. The signals x, y, z, are fed to respective inputs of a display device 5, consisting for example of an oscillograph or memory display device, and they execute the plotting of the $\bar{R}$ vector at the $K\Delta t$ time, in modulus, argument and application point. This procedure is repeated for each $K\Delta t$ By using suitable threshold signals this elaborating and plotting procedure automatically starts as soon as the transducing member T set is urged and automatically stops when the biasing on the transducing members T ends. The aforesaid threshold is adjustable and it may be adapted to the type of the analysed phenomena. This analysis of the forces acting on the plane z-y may be carried out in an analogous manner on the perpendicular plane z-x provided to suitable locate some switches.

Figure 2:
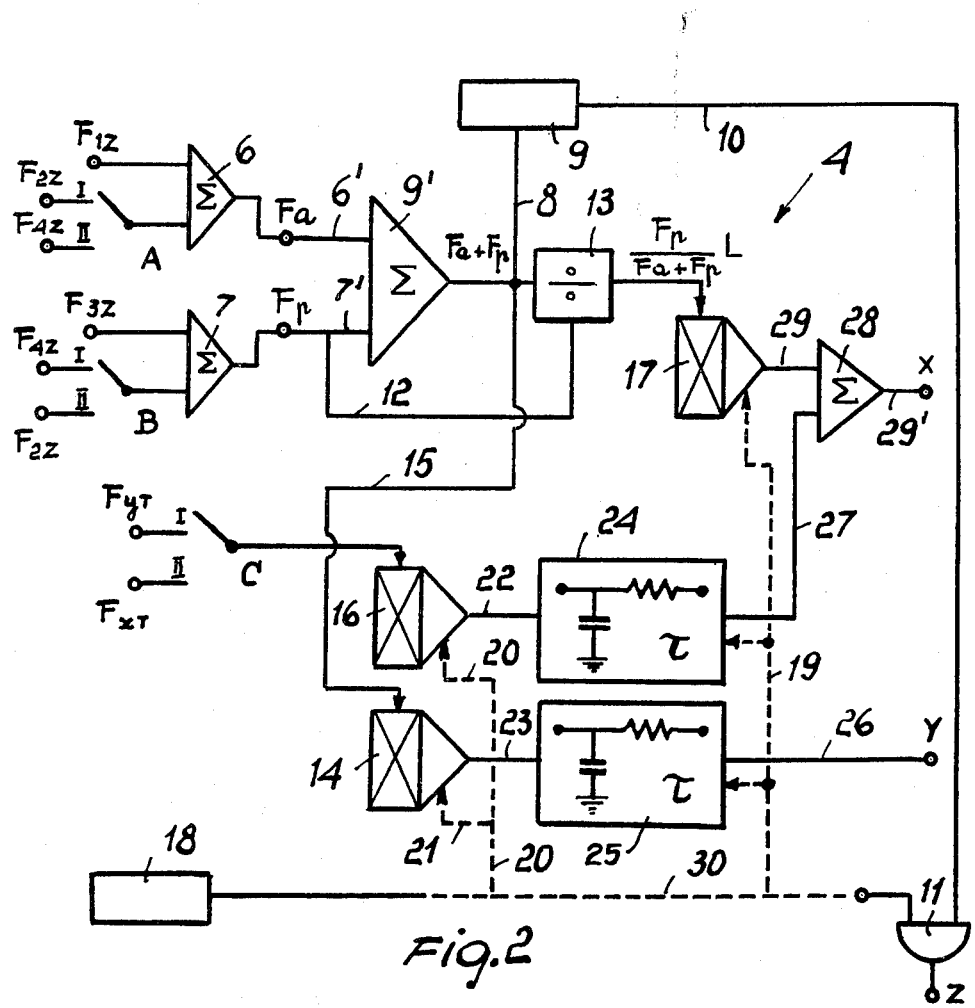
FIG. 2 is a schematic circuit diagram of the apparatus of the present invention.

It is believed that the above description is sufficient for understanding the hybrid elaborating means of the present invention which is illustrated in more detail in FIG. 2 to which reference is now made. With the switches A, B, C in the I position, the analysis in the sagittal plane S—S (FIG. 1A) may be carried out. In the II position the analysis in the front plane F—F (FIG. 1A) is carried out in an analogous manner. If it is desired to carry out the analysis in the sagittal plane (switches A, B, C in the I position), then the summing devices 6 and 7 provide respectively the aforesaid signals $F_a = F_{1z} + F_{2z}$ and $F_p = F_{3z} + F_{4z}$. The $F_a$ and $F_p$ signals are fed through the leads 6' and 7' respectively to a summing devcie 9' which provides the $R_z = F_a + F_p$ signal. This signal is fed from one side to a threshold circuit 9 which locks, by means of the connection 10 and the AND gate 11, the Z axis until the signal exceeds an at will adjustable threshold value and, on the other side it is fed together the $F_p$ signal through the lead 12 to the input of a dividing circuit 13 which executes the operation $[F_p/(F_a + F_p)] \cdot L$ and then provides a y signal which represents the coordinate of the vector $\bar{R}$ application point. The $F_a + F_p$ signal is also fed to a sample-hold circuit 14 through the lead 15. As shown in FIG. 2, other two sample-hold circuits 16 and 17 respectively are provided. The sample-hold circuits 17, 16, 14 receive respectively the y signal (which is the coordinate of the vector $\bar{R}$ application point), the $R_y$ signal (which is the vector $\bar{R}$ horizontal component) and the $R_z$ signal (which is the vector $\bar{R}$ vertical component). Said circuits 17, 16, 14 are driven by an adjustable clocking circuit 18 to which said circuits are respectively connected by means of leads 19, 20, 21 and which, at $\Delta t$ time intervals, sample and hold the value of said three signals. The outputs 16 and 14 go respectively by means of leads 22 and 23 to RC circuits 24, 25 which are perfectly calibrated and suitably clocked by the clocking device 18. The RC circuit 24, 25 output signal is therefore an exponential signal which asymptotically goes to the value imposed by the circuits 16 and 14. The output of the circuit 25 directly goes, through the lead 26, to the oscillograph Y axis. The RC circuit 24 output is taken through the lead 27 and fed to an input of a two input summing device 28 to the other input of which the output of the samplehold circuit 17 is fed through the lead 29. The summing device output 28 is directly fed through the lead 29' to the oscillograph X axis (not shown in FIG. 2). Then the clocking device 18 sends suitable signals, through the lead 30 connected to the other input of the AND gate 11, to the oscillograph z axis for suitably blanking said z axis.

Figure 3:
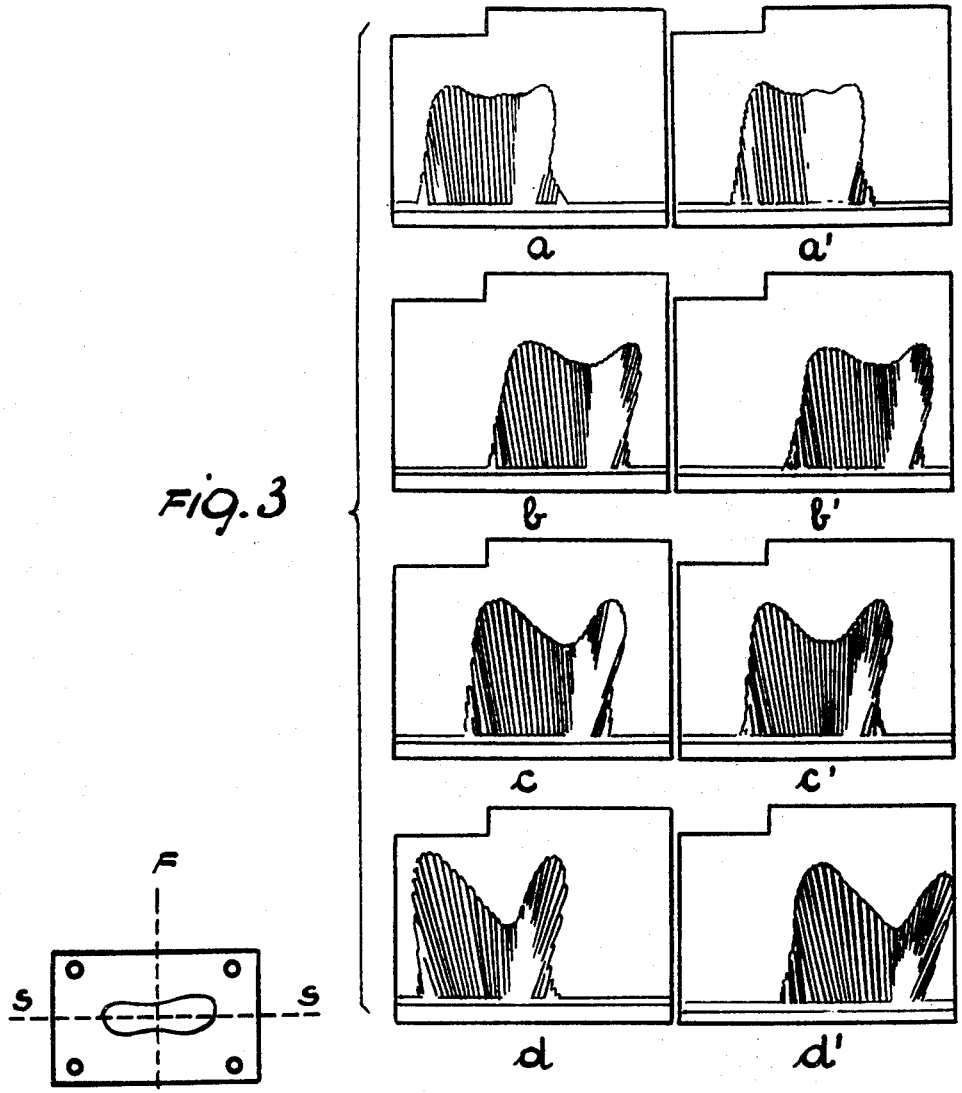
FIGS. 3 and 4 are typical vectorial diagrams indicative of the man locomotive functionality, which diagrams have been obtained from subjects by using the apparatus of the present invention.
Figure 4:
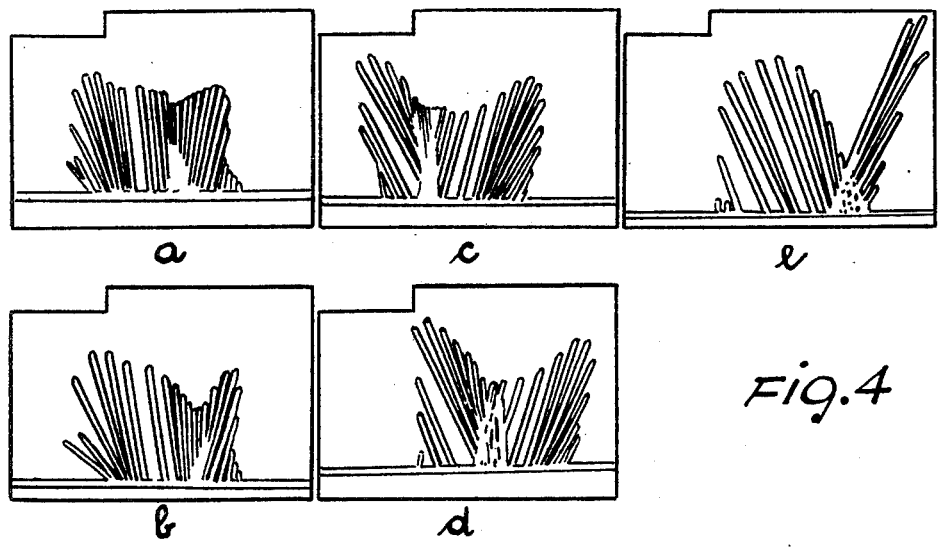

From the above description it may be seen that the hybrid elaborating means 4 elaborates the signals and provides the in-line representation of the vectorial diagram corresponding to the components of the forces exercised by the subject on the platform 2. In FIGS. 3 and 4 two typical series of vectorial diagrams obtained as previously described are illustrated. More specifically FIG. 3 shows the diagrams for a normal subject. The letters a, b, c, d and a', b', c', d' represent respectively the diagrams of the right and left feet of a normal subject, said diagrams being plotted for step frequencies of 80, 88, 100, 120 steps/minute. As shown in FIG. 3, the right and left foot diagrams are substantially coincident. On the contrary FIG. 4 shows the diagrams obtained from a pathological subject with poliomyelitis posthuma.

More specifically the diagrams a, b of FIG. 4 are those of the right leg, obtained with a frequency of 88 and 120 steps/minute respectively. The diagrams c, d and e of FIG. 4 are those of the left leg obtained with a frequency of 80, 88, 120 steps/minute respectively. In these diagrams one may observe clear poliomyelitis posthuma prevailing at the left leg on which the subject bore a protective device.

From the above description it appears that the present invention provides a man locomotive functionality evaluating apparatus which completely achieves the aforesaid objects. More specifically from extensive experimental tests it has been established that the described vectorial diagrams representation is strictly reliable and exactly repetible and allows for a recording of the functional damages of the man locomotive apparatus which is similar to the recording provided by the ECG and EMG for the damages of the cardiac and muscular systems respectively.

While the invention apparatus has been developed and described in connection with the biomedical field it is to be understood that said apparatus may be used in other production and technological fields and in all the cases in which it is requested a qualitatively strict recording of the dynamic interaction of a body revolving or slipping on ground or on any surface.

I claim:

1. A human locomotive functionality evaluating apparatus comprising a substantially rigid platform adapted to support a subject walking thereonto and exercising on said platform a force and/or pressure due to said walking; a plurality of force and/or pressure transducing members operatively associated with said platform and adapted to provide a corresponding multiplicity of electrical signals representative of said force and/or pressure on said platform, said apparatus being characterized in that it further comprises a hybrid processor circuitally connected to said plurality of transducing members and adapted to on-line convert onto an output display means the time-space representation of the projection on a plane of the resultant of the forces and/or pressures acting on said platform due to said walking of said subject thereonto, said hybrid processor comprising first and second RC circuit means operatively connected to outputs of sample-hold circuit means, said RC circuit means being driven by clock means and being adapted to provide at the outputs thereof an exponential signal asymptotically going to a value imposed by said sample-hold circuit means.

2. Apparatus according to claim 1, characterized in that it comprises summing means to sum the output of one of said sample-hold means and the output of one of said RC circuit means.

* * * * *